(12) United States Patent
Chen

(10) Patent No.: US 6,552,109 B1
(45) Date of Patent: Apr. 22, 2003

(54) GELATINOUS ELASTOMER COMPOSITIONS AND ARTICLES

(75) Inventor: John Y. Chen, Pacifica, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 0 days.

(21) Appl. No.: 08/612,586

(22) Filed: Mar. 8, 1996

Related U.S. Application Data

(63) Continuation-in-part of application No. PCT/US94/04278, filed on Apr. 19, 1994, application No. PCT/US94/07314, filed on Jun. 27, 1994, application No. 08/288,690, filed on Aug. 11, 1994, now Pat. No. 5,633,286, application No. 08/581,188, filed on Dec. 29, 1995, now abandoned, application No. 08/581,191, filed on Dec. 29, 1995, now Pat. No. 5,760,117, and application No. 08/581,125, filed on Dec. 29, 1995, now Pat. No. 5,962,572.

(51) Int. Cl.[7] .............................. C08J 5/02; C08J 51/00; C08K 5/01; B61C 15/00

(52) U.S. Cl. ..................... 524/270; 132/321; 442/59; 428/319.3; 428/319.7; 428/319.9; 428/378; 428/441; 428/462; 428/521; 428/537.1; 428/688; 174/137 A; 174/137 B; 524/474; 524/476; 524/490; 524/505

(58) Field of Search ............................ 132/321; 442/59; 428/319.3, 319.7, 319.9, 378, 441, 462, 521, 537.1, 688; 174/137 A, 137 B; 524/505, 474, 490, 476; 525/95, 98

(56) References Cited

U.S. PATENT DOCUMENTS

| | | | | |
|---|---|---|---|---|
| 3,485,787 A | | 12/1969 | Haefele | 524/474 |
| 3,676,387 A | | 7/1972 | Lindlof | 524/487 |
| 3,827,999 A | | 8/1974 | Crossland | 524/500 |
| 3,860,013 A | | 1/1975 | Czapor | 132/91 |
| 3,935,338 A | | 1/1976 | Robertson | 427/207 |
| 4,001,167 A | | 1/1977 | Tungseth | 524/476 |
| 4,136,699 A | | 1/1979 | Collins | 604/387 |
| 4,151,057 A | | 4/1979 | St. Clair | 522/110 |
| 4,176,240 A | | 11/1979 | Sabia | 174/23 C |
| 4,259,540 A | | 3/1981 | Sabia | 174/23 C |
| 4,369,284 A | * | 1/1983 | Chen | 524/505 |
| 4,432,607 A | | 2/1984 | Levy | 350/96.34 |
| 4,492,428 A | | 1/1985 | Levy | 350/96.3 |
| 4,618,213 A | * | 10/1986 | Chen | 524/505 |
| 4,643,924 A | | 2/1987 | Uken | 428/35 |
| 4,690,831 A | | 9/1987 | Uken | 427/44 |
| 4,692,371 A | | 9/1987 | Morman | 428/244 |
| 4,709,982 A | | 12/1987 | Corne | 524/505 |
| 4,718,678 A | | 1/1988 | Vansant | 277/1 |
| 4,741,940 A | | 5/1988 | Reed | 428/68 |
| 4,822,834 A | | 4/1989 | Blevins | 524/427 |
| 4,842,931 A | | 6/1989 | Zook | 428/354 |
| 4,865,905 A | | 9/1989 | Uken | 428/220 |
| 4,880,878 A | | 11/1989 | Himes | 525/89 |
| 4,883,196 A | | 11/1989 | Sieverding | 524/480 |
| 4,900,877 A | | 2/1990 | Dubrow | 174/35 |
| 4,942,270 A | | 7/1990 | Gamarra | 174/93 |
| 5,066,259 A | | 11/1991 | Acker | 446/385 |
| 5,088,734 A | | 2/1992 | Glava | 273/735 |
| 5,098,421 A | | 3/1992 | Zook | 604/367 |
| 5,149,736 A | | 9/1992 | Gamarra | 524/490 |
| 5,153,254 A | * | 10/1992 | Chen | 524/505 |
| 5,167,649 A | | 12/1992 | Zook | 604/307 |
| 5,191,752 A | | 3/1993 | Murphy | 54/44.5 |
| 5,262,468 A | * | 11/1993 | Chen | 524/505 |
| 5,313,019 A | * | 5/1994 | Brusselmans et al. | 174/83 |
| 5,330,452 A | | 7/1994 | Zook | 604/307 |
| 5,334,646 A | * | 8/1994 | Chen | 428/521 |
| 5,336,708 A | * | 8/1994 | Chen | 132/321 |
| 5,479,952 A | | 1/1996 | Zachariades | 132/321 |
| 5,508,334 A | * | 4/1996 | Chen | 524/505 |
| 5,559,265 A | | 9/1996 | Love | 558/177 |
| 5,618,882 A | | 4/1997 | Hammond | 525/92 D |
| 5,633,286 A | * | 5/1997 | Chen | 524/505 |

FOREIGN PATENT DOCUMENTS

| | | |
|---|---|---|
| GB | 1268431 | of 0000 |
| WO | WO 9005166 | * 5/1990 |

OTHER PUBLICATIONS

"Properties of Oriented Block copolymers", A. Skoulios, Journal of Polymer Science: Polymer Symnposium 58, 369–379 (1977).

"Styrene–Diene Triblock Copolymers: Orientation Conditions and Mechanical Properties of The Oriented Materials" A. Weill and R. Pixa, Journal of Polymer Science Polymer Symposium 58, 381–394 (1977).

SC:1102–89 Shell Chemical Technical Bulletin "KRATON® Thermoplastic Rubber in oil gels" Apr. 1989.

Adhesion of Viscoelastic Materials to Rigid Substrates Proc. Roy. Soc. A. 310, 433–448 (1969) Printed in Great Britain.

Allen et al, Comprehensive Polymer Science—vol. 7; 1994; p. 416–431.

Kirk–Othmer; Encyclopedia of Chemical Technology; 1994; 4th Edition; p. 17–37.

Garder, William; Gardner's Chemical Synonyms and Trade Names; 1994.

Holden et al; Thermoplastic Elastomers; 2nd Edition; 1996; Chapter 1—p. 1–26; Chapter 3—p. 27–70; Chapter 4—p. 71–100.

\* cited by examiner

*Primary Examiner*—Herbert J. Lilling

(57) ABSTRACT

Novel gelatinous compositions and articles are formed from an intimate melt blend admixture of one or more of a high viscosity poly(styrene-ethylene-butylene-styrene), poly (styrene-ethylene-ethylene-propylene-styrene), poly (styrene-ethylene-butylene)$_n$, and poly(styrene-ethylene-propylene)$_n$ triblock and branched copolymers and high levels of a plasticizing oil.

12 Claims, No Drawings

GELATINOUS ELASTOMER COMPOSITIONS AND ARTICLES

ORIGINS OF INVENTION AND RELATED APPLICATIONS

This application is a continuation-in-part of the following applications: U.S. Ser. Nos. PCT/US94/04278 filed Apr. 19, 1994 (published May 26, 1995 No. WO95/13851); PCT/US94/07314 filed Jun. 27, 1994 (published Jan. 4, 1996 No. WO96/00118); USSN 08/288,690 filed Aug. 11, 1994, now U.S. Pat. No. 5,633,286; USSN 08/581,188 filed Dec. 29, 1995, now abandoned; USSN 08/581,191 filed Dec. 29, 1995, now U.S. Pat. No. 5,760,117; USSN 08/581,125 filed Dec. 29, 1995, now U.S. Pat. No. 5,962,572.

FIELD OF THE INVENTION

The present invention relates to useful gelatinous elastomer compositions and articles.

BACKGROUND OF THE INVENTION

This application is based upon subject matters described in earlier filed and copending related applications and patents (see Related Applications above) which are specifically incorporated herein by reference.

As taught in related U.S. Pat. No. 4,369,284, No. 4,618,213 and No. 5,153,254, oil extended thermoplastic block copolymers of the prior art suffer certain poor properties. Shell Technical Bulletin No. SC 65-75 teaches the use of low viscosity poly(styrene-ethylene-butylene-styrene) triblock copolymers (Kraton G 1650 and G 1652) with Brookfield Viscosities of 1,500 and 550 cps (viscosity being measured for a solution of 20 weight percent solids in toluene at 250° C.) plasticized with oil, the compositions obtained trend to rupture and crumble when submitted to moderate shearing stress conditions.

SUMMARY OF THE INVENTION

The advantages and inherent properties of the gelatinous elastomer compositions (herein interchangeably refer to as "gelatinous compositions" or simply as "gel compositions" or more simply as "gels") and articles of the invention are many. The gel compositions exhibits high dimensional stability, crack, tear, craze, and creep resistance, excellent tensile strength and high elongation, long service life under stress and capable of repeated handling, excellent processing ability for cast molding, non-toxic, nearly tasteless and odorless, extremely soft and strong, highly flexible, possessing elastic memory, substantially with little or no plasticizer bleedout. The gel can also be made transparent. The desirable combination of physical properties are unexpected.

In a first embodiment, the composites of the invention comprises a thermoplastic, heat formable and heat reversible gelatinous elastomer composition, G, which is formed into a composite by heat and interlocked with one or more of a selected substrate material, M, said gelatinous elastomer composition formed from (i) 100 parts by weight of one or a mixture of two or more of a hydrogenated styrene isoprene/butadiene block copolymer(s) and from (ii) about 300 to about 1,600 parts by weight of a plasticizing oil; said gelatinous elastomer compositions characterized by a gel rigidity of from about 20 to about 800 gram Bloom; wherein said block copolymers have the general configuration A-B-A wherein A is a glassy polymer end block segment of polystyrene and B is an elastomeric polymer center block segment of (ethylene-ethylene-propylene) and said gel being in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity of from about 20 to about 800 gram Bloom.

More generally, the invention comprises thermoplastic, heat formable and heat reversible gelatinous elastomer compositions and articles formed from (I) 100 parts by weight of one or more hydrogenated styrene block copolymers having 2-methyl-1,3-butadiene and 1,3-butadiene blocks of the formula poly(styrene-ethylene-ethylene-propylene-styrene) and optionally in combination with (II) a selected amount of one or more selected polymer or copolymer; (III) from about 300 to about 1,600 parts by weight of a plasticizing oil; said gelatinous elastomer compositions being characterized by a gel rigidity of from about 20 to about 800 gram Bloom.

Useful articles can be formed from the gelatinous elastomer compositions of the invention, including molded articles, composites (gel compositions "interlocked" with various substrates), articles having sticking and non-sticking properties, strong oriented gel compositions as view in polarized light etc.

The various aspects and advantages of the invention will become apparent to those skilled in the art upon consideration of the accompanying disclosure.

DESCRIPTION OF THE PREFERRED EMBODIMENTS

Gel compositions useful in the present invention are described in my earlier patents Nos. 4,369,284; 4,618,213; 5,153,254; 5,239,723; 5,262,468; 5,324,222; 5,334,646; 5,336,708; 5,475,890; 5,508,334; 5,624,294; 5,633,286; and 5,655,947 which are incorporated herein by reference.

The polymers useful in forming the gel compositions of the invention comprises high viscosity triblock and branched copolymers. The triblock copolymers have the general configuration A-B-A wherein each A is a glassy polymer end block segment of polystyrene and B is a elastomeric polymer center block segment of poly(ethylene-butylene), poly(ethylene-propylene) or poly(ethylene-ethylene-propylene). The useful high viscosity branched copolymers have the general configuration (A-B)$_n$ wherein A is polystyrene and B is (ethylene-butylene), (ethylene-propylene) or (ethyleneethylene-propylene) and the subscript n is an number. The B and A portions of the triblock and branched copolymers are incompatible and form a two-phase system consisting of sub-micron domains of glassy polystyrene interconnected by flexible B chains. These domains serve to crosslink and reinforce the structure. This physical elastomeric network structure is reversible, and heating the polymer above the softening point of polystyrene temporarily disrupt the structure, which can be restored by lowering the temperature.

The most preferred gels can be prepared by melt blending an admixture comprising: (I) 100 parts by weight of one or more of a high viscosity triblock or branched copolymers or a mixture of two or more of poly(styrene-ethylene-ethylene-propylene-styrene), poly(styrene-ethylene-butylene-styrene), poly(styrene-ethylene-propylene-styrene), (styrene-ethylene-propylene)$_n$, (styrene-ethylene-butylene)$_n$, and optionally in combination with (II) a selected amount of one or more polymer or copolymer selected from the group consisting of poly(styrene-butadiene-styrene), poly(styrene-butadiene), poly(styrene-isoprene-styrene), poly(styrene-isoprene), poly(styrene-ethylene-propylene), poly(styrene-ethylene-ethylene-propylene-styrene) poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, branched or star-shaped, or multiarm copolymer; and (III) from about 300 to about 1,600 parts by weight of an plasticizing oil.

As used herein, the liner triblock copolymers poly(styrene-ethylene-ethylene-propylene-styrene) is denoted by "SEEPS", poly(styrene-ethylene-butylene-styrene) is denoted by "SEBS", poly(styrene-ethylene-propylene-styrene) is denoted by "SEPS"; and the branched copolymers poly(styrene-ethylene-propylene)$_n$ is denoted by "(SEP)$_n$", and poly(styrene-ethylene-butylene)$_n$ is denoted by "(SEB)$_n$". Branched copolymers are often times conventionally referred to as radial or star-shaped polymers.

Gel compositions of the invention are characterized by gel rigidities of from less than about 20 gram Bloom to about 700 gram Bloom and higher. As used herein, the term "gel rigidity" in gram Bloom is determined by the gram weight required to depress a gel a distance of 4 mm with a piston having a cross-sectional area of 1 square centimeter at 23° C.

It should be noted that when the A to B ratio falls substantially below 31:69, various properties such as elongation, tensile strength, tear resistance and the like can decrease while retaining other desired properties, such as gel rigidity, flexibility, elastic memory.

The high viscosity triblock, radial, star-shaped, and multiarm copolymers in (I) which are suitable for use in the present invention has a typical Brookfield Viscosity value of a 20 weight percent solids solution in toluene at 25° C. of at least about 1,800 cps, and preferably about 2,000 cps or higher. Typically, the Brookfield Viscosity values can range from at least about 1,800 to about 16,000 cps and higher. More typically, the Brookfield Viscosity values can range from at least about 1,800 cps to about 40,000 cps and higher. Still more typically, the Brookfield Viscosity values can range from at least about 1,800 cps to about 80,000 cps and higher. Due to structural variations between the triblock, radial, star-shaped, and multiarm copolymers, the high viscosity branched copolymers useful in the invention, typically, may exhibit a lower Brookfield Viscosity value than its counterpart triblock copolymers. However, when the triblock copolymers are considered as branched, then at equal branch lengths, the solution viscosities of the triblock copolymers and branched copolymers are about the same or equivalent. In other words, the typical Brookfield Viscosity values for branched copolymers of a 20 weight percent solids solution in toluene at 25° C. can be less than their counterpart triblock copolymers.

In all cases, the molecular chain lengths (molecular weights) of the triblock and branch copolymers must be sufficient to meet the high solution Brookfield Viscosities requirements described herein that is necessary for making the extremely soft and strong gel compositions.

The high viscosity triblock and branched copolymers: SEEPS, SEBS, SEPS, (SEB)$_n$, and (SEP)$_n$ can be measured under varying conditions of weight percent solution concentrations in toluene. The most preferred and useful triblock and branched copolymers selected have Brookfield Viscosity values ranging from about 1,800 cps to about 80,000 cps and higher when measured at 20 weight percent solution in toluene at 25° C., about 4,000 cps to about 40,000 cps and higher when measured at 25 weight percent solids solution in toluene. Typical examples of Brookfield Viscosity values for branched copolymers (SEB)$_n$ and (SEP)$_n$ at 25 weight percent solids solution in toluene at 25° C. can range from about 3,500 cps to about 30,000 cps and higher; more typically, about 9,000 cps and higher. Other preferred and acceptable triblock and branched copolymers can exhibit viscosities (as measured with a Brookfield model RVT viscometer at 25° C.) at 10 weight percent solution in toluene of about 400 cps and higher and at 15 weight percent solution in toluene of about 5,600 cps and higher. Other acceptable triblock and branched copolymers can exhibit about 8,000 to about 20,000 cps at 20 weight percent solids solution in toluene at 25° C. Examples of most preferred high viscosity triblock and branched copolymers can have Brookfield viscosities at 5 weight percent solution in toluene at 30° C. of from about 40 to about 50 cps and higher. While less preferred polymers can have a solution viscosity at 10 weight percent solution in toluene at 30° C. of about 59 cps and higher.

The high viscosity triblock, radial, star-shaped, and multiarm copolymer of the invention can have a broad range of styrene end block to ethylene and butylene center block ratio of about 20:80 or less to about 40:60 or higher. Examples of high viscosity triblock copolymers that can be utilized to achieve one or more of the novel properties of the present invention are styrene-ethylene-butylene-styrene block copolymers (SEBS) available from Shell Chemical Company and Pecten Chemical Company (divisions of Shell Oil Company) under trade designations Kraton G 1651, Kraton G 1654X, Kraton G 4600, Kraton G 4609 and the like. Shell Technical Bulletin SC:1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68-79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity SEBS triblock copolymers includes Kuraray's SEBS 8006 which exhibits a solution viscosity at 5 weight percent at 30° C. of about 51 cps. Kuraray's 4055 SEEPS (styrene-ethylene/ethylene-propylene-styrene) block polymer made from hydrogenated styrene isoprene/butadiene block copolymer or more specifically made from hydrogenated styrene block polymer with 2-methyl-1,3-butadiene and 1,3-butadiene which exhibits a viscosity at 5 weight percent solution in toluene at 30° C. of about 90 mPa-S, at 10 weight percent about 5800 mPa-S. Kuraray's 2006 SEPS polymer exhibits a viscosity at 20 weight percent solution in toluene at 30° C. of about 78,000 cps, at 5 weight percent of about 27 mPa-S, at 10 weight percent of about 1220 mPa-S, and at 20 weight percent 78,000 cps. Kuraray SEPS 2005 polymer exhibits a viscosity at 5 weight percent solution in toluene at 30° C. of about 28 mPa-S, at 10 weight percent of about 1200 mPa-S, and at 20 weight percent 76,000 cps. Other grades of SEBS, SEPS, $(SEB)_n$, $(SEP)_n$ polymers can also be utilized in the present invention provided such polymers exhibits the required high viscosity. Such SEBS polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's SEBS polymer 8006 the S:EB weight ratio is about 35:65. In the case of Kuraray's 2005, 2006, and 4055 the and S:EEP weight ratios are 20, 35 and 30 respectively. Much like S:EB ratios of SEBS and $(SEB)_n$, the S:EP ratios of very high viscosity SEPS, $(SEP)_n$ copolymers are expected to be about the same and can vary broadly.

The S:EB, S:EP weight ratios of high viscosity SEBS, SEPS, $(SEB)_n$, and $(SEP)_n$ useful in forming the gel compositions of the invention can range from lower than about 20:80 to above about 40:60 and higher. More specifically, the values can be 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49 and etc. Other ratio values of less than 19:81 or higher than 51:49 are also possible. Broadly, the styrene block to elastomeric block ratio of the high viscosity triblock, radial, star-shaped, and multiarm copolymers of the invention is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and most preferably about 33:67. In accordance with the present invention, triblock copolymers such as Kraton G 1654X having ratios of 31:69 or higher can be used and do exhibit about the same physical properties in many respects to Kraton G 1651 while Kraton G 1654X with ratios below 31:69 may also be use, but they are less preferred due to their decrease in the desirable properties of the final gel.

Other polymers and copolymers (in major or minor amounts) can be selectively melt blended with one or more of the high viscosity polymers as mentioned above without substantially decreasing the desired properties; these (III) polymers include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers, (SEPS) styrene-ethylene-propylene-styrene block copolymers, $(SB)_n$ styrene-butadiene and $(SEB)_n$, $(SEBS)_n$, $(SEP)_n$, $(SI)_n$ styrene-isoprene multi-arm, branched or star-shaped copolymers and the like. Still, other (III) polymers include homopolymers which can be utilized in minor amounts; these include: polystyrene, polybutylene, polyethylene, polypropylene and the like.

Representative plasticizer oil gels (polymer+oil) of the invention include: (a) Kraton G 1651, G 1654X gels; (b) Kraton G 4600 gels; (c) Kraton G 4609 gels; other suitable high viscosity polymer and oil gels include: (d) Tuftec H 1051 gels; (e) Tuftec H 1041 gels; (f) Tuftec H 1052 gels; (g) Kuraray SEEPS 4055 gel; (h) Kuraray SEBS 8006 gel; (i) Kuraray SEPS 2005 gel; (j) Kuraray SEPS 2006 gel, and (k) Gels made from blends (polyblends) of (a)-(h) with other polymers and copolymers include: (1) SEBS-SBS gels: (2) SEBS-SIS gels; (3) SEBS-(SEP) gels; (4) SEBS-$(SEB)_n$ gels; (5) SEBS-$(SEB)_n$ gels; (6) SEBS-$(SEP)_n$ gels; (7) SEBS-$(SI)_n$ gels; (8) SEBS-(SI) multiarm gels; (9) SEBS-$(SEB)_n$ gels; (10) $(SEB)_n$ star-shaped copolymer gels; (11) gels made from blends of (a)-(k) with other homopolymers include: (12) SEBS/polystyrene gels; (13) SEBS/polybutylene gels; (14) SEBS/polyethylene gels; (14) SEBS/polypropylene gels; (16) SEP/SEBS oil gels (17), SEP/SEPS oil gels (18), SEP/SEPS/SEB oil gels (19), SEPS/SEBS/SEP oil gels (20), SEB/SEBS (21), EB-EP/SEBS (22), SEBS/EB (23), SEBS/EP (24), (25) $(SEB)_n$ gels, (26) $(SEP)_n$ gels and the like.

Representative examples of commercial elastomers that can be formed with plasticizing oils in combination with the high viscosity triblock and branched copolymers described above into suitable gels for use in making the gel compositions of the invention: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158, D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940. Kuraray's SEEPS, SEP/SEPS or SEP/SEB/SEPS Nos. 1001, 1050, 2002, 2003, 3023, 2007, 2043, 2063, 2050, 2103, 2104, 2105, 4033 (SEEPS), 4045 (SEEPS), 8004 (SEBS), 8007, and the like.

Plasticizers particularly preferred for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly (ethylene/butylene/styrene) with epoxidized polyisoprene and poly(ethylene/butylene) with epoxidized polyisoprene: Example of such polybutenes include: L-14 (320 Mn), L-50

(420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27-37 cst @ 100oF Viscosity), H-300E (635-690 cst @ 210oF Viscosity), Actipol E6 (365 Mn), E16 (973 Mn), E23 (1433 Mn), Kraton L-1203, EKP-206, EKP-207, HPVM-2203 and the like. Example of various commercially oils include: ARCO Prime (55, 70, 90, 200, 350, 400 and the like), Duraprime and Tufflo oils (6006, 6016, 6016M, 6026, 6036, 6056, 6206, etc), other white mineral oils include: Bayol, Bernol, American, Blandol, Drakeol, Ervol, Gloria, Kaydol, Litetek, Lyondell (Duraprime 55, 70, 90, 200, 350, 400, etc), Marcol, Parol, Peneteck, Primol, Protol, Sontex, and the like.

The Kuraray SEPTON 4000 series block polymers: 4033, 4055, 4045, and the like useful in making the gels of the instant invention are made from hydrogenated styrene isoprene/butadiene styrene block copolymer or more specifically made from hydrogenated styrene block polymer with 2-methyl-1,3-butadiene and 1,3-butadiene. Such poly (styrene-isoprene/butadiene-styrene) polymers, depending on the butadiene structure, when hydrogenated will result in "(SEB/EPS)" or reading the other way "(SEP/EBS)". In cases where the butadiene structures are controlled, it is appropriate to denote (SEB/EPS) as (SE/EPS) where E/EP is ethylene-ethylene-propylene or more simply as (SEEPS) to indicate that the ethylene (E) of the ethylene-butylene (EB) segment of the midblock (EB/EP) of the (SEB/EPS) block polymer is substantially greater than butylene (B) and the amount of (E) can be sufficient so as to exhibit ethylene crystallinity.

Generally, plasticizing oils with average molecular weights less than about 200 and greater than about 700 may also be used (e.g. H-300 (1290 Mn)).

The gel compositions of the invention can also be made into composites. The gels may be made non-adhearing, non-sticking, (non-tacky), by incorporating an advantage amount of stearic acid (octadecanoic acid) or metal stearates (e.g., calcium stearate, magnesium sterate, zinc stearate, etc.).

An advantage of making non-sticking, non-tacky gels is the use of waxes, stearic acid and waxes, metal sterate and waxes, metal sterate and stearic acid. The use of stearic acid alone do not reduce tack. The amount of stearic acid is also important. As an example, ratio of 200 grams stearic acid to 2,000 gram of SEBS (a ratio of 0.1) will result in spotted tack reduction on the surface of the gel. A ratio of 250 to 2,000 will result in spotted crystallized regions on the surface of the gel or spotted tack reduction. A ratio of 300 to 2,000 will result in complete tack reduction with large stearic acid crystallized regions on the surface of the gel. When microcrystalline waxes are incorporated together with stearic acid, the crystallization of stearic acid completely disappears from the surface of the gel. For example excellent result is achieved with 200 grams of stearic acid, 150 grams of microcrystalline wax and 2,000 grains of SEBS. The same excellent results is achieved when SEBS is adjusted to 3,000 grams, 4,000 grams, etc. The same result is achieved with SEPS, $(SEB)_n$, $(SEP)_n$ polymers.

The present invention also provides oriented gels with improved high strength alignment properties as evidenced by optical techniques such as viewing oriented gel in plane-polarized light. Oriented gels exhibit birefringence in the relaxed unextended state. Oriented gels with improved strength are suitable for use as dental floss since they do not break as easily as un-oriented gels of the same rigidity.

The oriented gels can also contain useful amounts of conventionally employed additives such as stabilizers, antioxidants, antiblocking agents, colorants, fragrances, flame retardants, flavors, other polymers in minor amounts and the like to an extend not affecting or substantially decreasing the desired properties of the invention.

Oriented gels aligned by controlled stretching during the gel's transition from a heated, extremely viscous, non melting, non flowing state and the cooled solid gel state produces strong gels which are found to have greater tensile strength than gels of the same rigidity which have not been stretched to a selected degree during its heating and cooling histories. Gels which are selectively stretched during its (non melt flowing) heated state and rapidly cooled by flowing air, cold liquid bath or in contact with a cool surface exhibit optical birefringence when viewed under plane-polarized light. The degree of stretching during the gels cooling history from the heated state can vary. Stretching of at least about 50% to more than about 1000% are of advantage to produce birefringence and stronger gels. Birefrigence is not observed in relaxed gels which do not undergo stretching during its heating and cooling histories. Slight to very strong birefringence are observed in relaxed gels which are stretched during their heating and cooling histories. It is evident that stressing the gel during its cooling history as it cools from the heated state produce unexpected stronger oriented gels. We therefore consider oriented gels to be a new and novel composition physically different from the less stronger gels formed without stressing during the gels cooling history and which do not show birefrigence in the relaxed state. Oriented gets may be formed in combination with various substrates such as described below. In past situations where in order to obtain stronger gel strength, gels with higher rigidities and lower plasticizer content must be used, it is now possible to make a oriented gel with the same plasticizer content having a higher useful gel strength.

The gel compositions and oriented gel compositions of the invention can be casted unto various substrates, such as open cell materials, metals, ceramics, glasses, and plastics, etc.; the molten gel composition is deformed as it is being cooled. Useful open-cell plastics include: polyamides, polyimides, polyesters, polyisocyanurates, polyisocyanates, polyurethanes, poly(vinyl alcohol), etc. Open-celled Plastic (sponges) suitable for use with the compositions of the invention are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The gel compositions denoted as "G" of the invention can be physically interlocked with a selected material denoted as "M" to form composites as denoted for simplicity by their combinations $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_n$, $G_nG_nM_n$, $G_nM_nG_nM_nM_n$, $M_nG_nM_nG_nM_nG_n$, $G_nG_nM_nM_nG_n$, $G_nG_nM_nG_nM_nG_n$, and the like or any of their permutations of one or more $G_n$ with $M_n$ and the like, wherein when n is a subscript of M, n is the same or different selected from the group consisting of foam, plastic, fabric, metal, concrete, wood, glass, ceramics, synthetic resin, synthetic fibers or refractory materials and the like; wherein when n is a subscript of G, n denotes the same or a different gel rigidity of from about 20 to about 800 gram Bloom). The gel compositions of the composites are formed from I, II, and III components described above.

Sandwiches of gel/material (i.e. gel-material-gel or material-gel-material, etc.) are ideal for use as shock absorbers, acoustical isolators, vibration dampers, vibration isolators, and wrappers. For example the vibration isolators can be use under research microscopes, office equipment, tables, and the like to remove background vibrations.

The gelatinous elastomer compositions and oriented gel compositions are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of SEBS, SEPS, $(SEB)_n$, $(SEP)_n$ or mixtures thereof used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the instant compositions in amounts of about 40 lbs or less to 10,000 lbs or more. For example, in a large vessel, inert gases can be employed for removing the composition from a closed vessel at the end of mixing and a partial vacuum can be applied to remove any entrapped bubbles. Stirring rates utilized for large batches can range from about less than 10 rpm to about 40 rpm or higher.

The oriented gelatinous elastomer composition of the invention is excellent for forming the strong gelatinous elastomer articles of the invention. The gelatinous elastomer articles can be formed by blending, injection molding, extruding and other conventional methods. For example, Shapes having various crossection can be extruded; and as the hot exudate is emerging from the extrusion die, the extradate can be stretched, pulled, twisted or in various manner stressed as it is rapidly placed in contact with cooling air, cool water bath, or other cooling media.

The gel compositions can also be formed directly into articles or remelted in any suitable hot melt applicator and extruded or spun into threads, bands, or other shapes.

The instant compositions is excellent for cast molding and the molded products have various excellent characteristics which cannot be anticipated form the properties of the raw components. Other conventional methods of forming the composition can be utilized.

The basis of this invention resides in the fact that one or more of a high viscosity triblock or branched copolymers or a mixture of two or more of such copolymers having styrene end block to elastomeric block ratio preferably within the contemplated range of from about 20:80 to about 40:60 and higher, more preferably from between about 31:69 to about 40:60 and higher when blended in the melt with an appropriate amount of plasticizing oil makes possible the attainment of gelatinous elastomer compositions having a desirable combination of physical and mechanical properties, notably high elongation at break of at least 1,600%, ultimate tensile strength of about at least $8 \times 10^5$ dyne/cm$^2$, low elongation set at break of substantially not greater than about 2%, tear resistance of at least $5 \times 10^5$ dyne/cm$^2$, substantially about 100% snap back when extended to 1,200% elongation, and a gel rigidity of substantially from about 20 gram to about 700 gram Bloom and higher.

More specifically, the gelatinous composition of the present invention exhibit one or more of the following properties. These are: (1) tensile strength of about $8 \times 10^5$ dyne/cm$^2$ to about $10^7$ dyne/cm$^2$ and greater; (2) elongation of about 1,600% to about 3,000% and higher; (3) elasticity modulus of about $10^4$ dyne/cm$^2$ to about $10^6$ dyne/cm$^2$ and greater; (4) shear modulus of about $10^4$ dyne/cm$^2$ to about $10^6$ dyne/cm$^2$ and greater as measured with a 1, 2, and 3 kilogram load at 23° C.; (5) gel rigidity of about less than about 20 gram Bloom to about 700 gram Bloom and higher as measured by the gram weight required to depress a gel a distance of 4 mm with a piston having a cross-sectional area of 1 square cm at 23° C.; (6) tear propagation resistance of at least about $5 \times 10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The gelatinous elastomer articles molded from the instant compositions have various additional important advantages in that they do not crack, creep, tear, crack, or rupture in flexural, tension, compression, or other deforming conditions of normal use; but rather the molded articles made from the instant composition possess the intrinsic properties of elastic memory enabling the articles to recover and retain its original molded shape after many extreme deformation cycles as compared to prior art triblock copolymer oil-extended compositions. In applications where low rigidity, high elongation, good compression set and excellent tensile strength are important, the instant gel compositions would be preferred.

The gelatinous elastomer compositions of the present invention are useful in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components. The compositions are also useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses may include as toys, optical uses (e.g. cladding for cushioning optical fibers from bending stresses) and various optical devices, as lint removers, dental floss, as tips for swabs, as fishing bate, as a high vacuum seal (against atmosphere pressure) which contains a useful amount of a mineral oil-based magnetic fluid particles, etc.

As an example of the versatility of use of the instant gel compositions, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions for the hand, wrist, finger, forearm, knee, leg, etc.

Another versatile use of the composition is dental flossing. The dental floss can be almost any shape so long as it is suitable for dental flossing. A thick shaped piece of the composition can be stretched into a thin shape and used for flossing. A thinner shaped piece would require less stretching, etc.

The instant compositions can be formed in any shape; the original shape can be deformed into another shape (to contact a regular or irregular surface) by pressure and upon removal of the applied pressure, the composition in the deformed shape will recover back to its original shape.

While preferred components and formulation ranges have been disclosed herein persons of skill in the art can extend these ranges using appropriate material according to the principles discussed herein. All such variations and deviations which rely on the teachings through which the present invention has advanced the art are considered to be within the spirit and scope of the present invention. The invention is further illustrated by means of the following illustrative embodiments, which are given for purpose of illustration only and are not meant to limit the invention to the particular components and amounts disclosed.

EXAMPLE I

A comparison was made between a low viscosity poly(styrene-ethylene-butylene-styrene) triblock copolymer having styrene end block to ethylene and butylene center block ratio below the range between 31:69 to 40:60 and a high viscosity poly(styrene-ethylene-butylene-styrene) triblock copolymer of the invention. Three different triblock copolymers were melt blended separately with a paraffinic white petroleum oil. Table I below shows the physical properties obtain with respect to each of the different viscosity and styrene to ethylene and butylene ratio triblock copolymer oil-blends tested.

The properties measured are as follows: Tear Propagation (ASTM D 19938 modified), Cracking (ASTM D 518 Method B modified), Tensile Strength (ASTM D 412 modified), Ultimate elongation (ASTM D 412 modified), Tensile Set (ASTM D 412 Modified), Compression Set (ASTM D 395 modified), Snap Back, and Hand Kneading (60 seconds). The methods of measurement are taught in United States patents Nos. 4,618,213 and 5,153,254; and, as well as, in copending applications Serial Nos. 705,711; 934,027 and 935,540.

TABLE I

| Formulation | S/EB Ratio[1] | Weight Parts | | |
|---|---|---|---|---|
| | | A | B | C |
| SEBS[2] | 28:72 | 100 | | |
| SEBS[3] | 29:71 | | 100 | |
| SEBS[4] | 33:67 | | | 100 |
| Paraffinic oil[5] | | 400 | 400 | 400 |
| Stabilizer[6] | | 2.5 | 2.5 | 2.5 |
| Breaking strength[7], dyne/cm$^2$ | | 4 × 10$^5$ | 4 × 10$^5$ | 4 × 10$^6$ |
| Tear propagation[8], dyne/cm$^2$ | | 8 × 10$^4$ | 7 × 10$^4$ | 1 × 10$^6$ |

TABLE I-continued

| Formulation | S/EB Ratio[1] | Weight Parts | | |
|---|---|---|---|---|
| | | A | B | C |
| Compression set[10] at 24 hours | | 81%$^R$ | 77%$^R$ | 0.0% |
| Rigidity, gram Bloom | | 1,536 | 1,520 | 360 |

[1]Styrene to ethylene and butylene ratio
[2]Shell Kraton G1650 having a Brookfield viscosity of 1,500 cps as measured for a 20% weight solids solution in toluene at 25° C.
[3]Shell Kraton G 1652 having a Brookfield viscosity of 550 cps as measured for a 20% weight solids solution in toluene at 25° C.
[4]Shell Kraton G 1651 having a Brookfield viscosity of 2,000 cps as measured for a 20% weight solids solution in toluene at 25° C.
[5]ARCO prime 200,
[6]Irganox 1010,
[7]ASTM D 412 modified,
[8]ASTM D 1938 modified,
[9]ASTM D 412 modified,
[10]ASTM D 2395 modified,
$^R$ruptured completely The results of Table I show drastically unacceptable poor properties of low viscosity triblock copolymers having styrene to ethylene and butylene ratios and low viscosity which are below the contemplated (preferred) range of the instant invention.

Comparisons of oil extended triblock copolymers have been described in Shell Chemical Company Technical Bulletin SC: 1102-89 (Apr. 1989) "KRATON®THERMOPLASTIC RUBBERS IN OIL GELS" which is incorporated herein by reference.

EXAMPLE II

One hundred parts by weight of a high viscosity poly(styrene-ethylene-butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tufflo 6024). Samples having the dimensions of 5 cm×5 cm×3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concessions are set forth in Table II below.

TABLE II

| Oil per 100 parts of Triblock copolymer | Gel Rigidity, gram Bloom |
|---|---|
| 360 | 500 |
| 463 | 348 |
| 520 | 280 |
| 615 | 240 |
| 635 | 220 |
| 710 | 172 |
| 838 | 135 |
| 1,587 | 54 |

EXAMPLE III

Example II was repeated except about 980 parts oil was used and the gel rigidity found to about 101 gram Bloom. Other properties measured were: tensile strength at break about 4.4×10$^6$ dyne/cm$^2$, elongation at break about 2,4470%, elasticity modulus about 3.5×10$^4$ dyne/cm$^2$, and shear modulus about $3.7 \times 10^4$ dyne/cm$^2$. The tensile strength, elongation, elasticity modules were measured with cross-head separation speed of 25 cm/minute at room temperature. The shear modulus was measured with a 1, 2, and 3 kilogram load at room temperature.

EXAMPLE IV

Example II was repeated except about 520 parts of a polybutene (Amoco Indopol H-300) was used and the gel rigidity found to be about substantially unchanged with respect to use of naphthenic oil alone.

EXAMPLE V

Example II was repeated except about 520 parts of a polypropene (Amoco C-60) was used and the gel rigidity found to be about substantially unchanged with respect to use of naphthenic oil alone.

EXAMPLE VI

Example II was repeated except about 520 parts of a polyterpene (Hercules Piccolyte S10) was used and the gel rigidity found to be about substantially unchanged with respect to use of naphthenic oil alone.

EXAMPLE VII

Example II was repeated except about 360 parts of a combined mixture of: 72 parts of a paraffinic oil (ARCO prime 200), 72 pars of a naphthenic oil (ARCO Tufflo 6014), 72 parts of a polybutene oligomer (Amoco Indopol H-200), 72 parts of a polypropene oligomer (Amoco Polypropene C-60), and 72 parts of a polyterpene oligomer (Hercules Piccolyte S10) was used and the gel rigidity found to be about substantially unchanged with respect to the use of naphthenic oil alone.

EXAMPLE VIII

Example III was repeated except 933 parts oil with 147 parts by weight of a high viscosity poly(styrene-ethylene-butylene-styrene) triblock copolymer containing 47 parts of a naphthenic process oil (Shell Kraton G 4609) having a styrene to ethylene and butylene ratio of about 33:67 was used and the physical properties were found to be about substantially unchanged with respect to the components used in Example III.

EXAMPLE IX

Example III was repeated except 933 parts oil with 147 parts by weight of a high viscosity poly(styrene-ethylene-butylene-styrene) triblock copolymer containing 47 parts of a paraffinic white petroleum oil (Shell Kraton G 4609) having a styrene to ethylene and butylene ratio of about 33:67 was used and the physical properties were found to be about substantially unchanged with respect to the components used in Example I.

EXAMPLE X

Example I was repeated except about 400 parts of oil was used and the properties measured were: tear propagation about $1.4 \times 10^6$ dyne/cm$^2$, no crack growth in 180° bend under 50 gram load for 5,000 hours at room temperature, tensile strength about $4 \times 10^6$ dyne/cm$^2$, elongation at break about 1,700%, tensile set about 0% at 1,200% elongation, compression set about 0% when tested under 5,000 gram load for 24 hours, and 100% snap back recovery after extension to 1,200%.

Examples XI-XIV-t below illustrate other modes of practice contemplated.

EXAMPLE XI

The procedure of Example II is repeated except Shell Kraton G 1651, poly(styrene-ethylene-butylene-styrene) triblock copolymer is used having a styrene end block to ethylene and butylene center block ratio of about 32:68 and the gel rigidity is found to be within the range of about 20 to about 700 gram Bloom.

EXAMPLE XII

The procedure of Example II is repeated except Shell Kraton G 1651, poly(styrene-ethylene-butylene-styrene) triblock copolymer, is used having a styrene end block to ethylene and butylene center block ratio of about 34:66 and the gel rigidity is found to be within the range of about 20 to about 700 gram Bloom.

EXAMPLE XIII

The procedure of Example II is repeated except Shell Kraton G 1651, poly(styrene-ethylene-butylene-styrene) triblock copolymer, is used having a styrene end block to ethylene and butylene center block ratio of about 36:64 and the gel rigidity is found to be within the range of about 20 to about 700 gram Bloom.

EXAMPLE XIV

The procedure of Example II is repeated except Shell Kraton G 1651, poly(styrene-ethylene-butylene-styrene) triblock copolymer, is used having a styrene end block to ethylene and butylene center block ratio of about 38:62 and the gel rigidity is found to be within the range of about 20 to about 700 gram Bloom.

EXAMPE XIV-a

The procedure of Example II is repeated except Shell Kraton G 1651, poly(styrene-ethylene-butylene-styrene) triblock copolymer, is used having a styrene end block to ethylene and butylene center block ratio of about 31:69 and the gel rigidity is found to be within the range of about 20 to about 800 gram Bloom.

EXAMPLE XIV-b

The procedure of Example II is repeated except Shell Kraton G 1651, poly(styrene-ethylene-butylene-styrene) triblock copolymer, is used having a styrene end block to ethylene and butylene center block ratio of about 37:63 and the gel rigidity is found to be within the range of about 20 to about 800 gram Bloom.

EXAMPLE XIV-c

The procedure of Example II is repeated except Shell Kraton G 1651, poly(styrene-ethylene-butylene-styrene) triblock copolymer, is used having a styrene end block to ethylene and butylene center block ratio of about 19:81 and the gel rigidity is found to be within the range of about 20 to about 800 gram Bloom.

EXAMPLE XIV-d

The procedure of Example II is repeated except Shell Kraton G 1651, poly(styrene-ethylene-butylene-styrene) triblock copolymer, is used having a styrene end block to ethylene and butylene center block ratio of about 20:80 and the gel rigidity is found to be within the range of about 20 to about 800 gram Bloom.

EXAMPLE XIV-e

The procedure of Example II is repeated except Shell Kraton G 1651, poly(styrene-ethylene-butylene-styrene) triblock copolymer is used having a styrene end block to ethylene and butylene center block ratio of about 38:62 and the gel rigidity is found to be within the range of about 20 to about 800 gram Bloom.

EXAMPLE XIV-f

The procedure of Example II is repeated except Shell Kraton G 1651, poly(styrene-ethylene-butylene-styrene) triblock copolymer, is used having a styrene end block to ethylene and butylene center block ratio of about 29:71 and the gel rigidity is found to be within the range of about 20 to about 800 gram Bloom.

EXAMPLE XIV-g

The procedure of Example II is repeated except Shell Kraton G 1651, poly(styrene-ethylene-butylene-styrene) triblock copolymer, is used having a styrene end block to ethylene and butylene center block ratio of about 26:74 and the gel rigidity is found to be within the range of about 20 to about 800 gram Bloom.

EXAMPLE XIV-h

The procedure of Example II is repeated except Shell Kraton G 1651, poly(styeene-ethylene-butylene-styrene) triblock copolymer, is used having a styrene end block to ethylene and butylene center block ratio of about 22:78 and the gel rigidity is found to be within the range of about 20 to about 800 gram Bloom.

EXAMPLE XIV-i

The procedure of Example II is repeated except Shell Kraton G 1651, poly(styrene-ethylene-butylene-styrene) triblock copolymer, is used having a styrene end block to ethylene and butylene center block ratio of about 25:75 and the gel rigidity is found to be within the range of about 20 to about 800 gram Bloom.

EXAMPLE XIV-j

The procedure of Example II is repeated except Shell Kraton G 1651, poly(styrene-ethylene-butylene-styrene) triblock copolymer, is used having a styrene end block to ethylene and butylene center block ratio of about 26:74 and the gel rigidity is found to be within the range of about 20 to about 800 gram Bloom.

EXAMPLE XIV-k

Example II is repeated except a high viscosity poly(styrene-ethylene-propylene-styrene) polymer having a S:EP ratio of 35:65 and a Brookfield Viscosity at 20 weight percent at 30° C. of about 78,000 cps is used and the gel rigidity found to be found to be within the range of about 20 to about 800 gram Bloom.

EXAMPLE XIV-l

Example II is repeated except a high viscosity poly(styrene-ethylene-propylene-styrene) polymer having a S:EP ratio of 20:80 and a Brookfield Viscosity at 20 weight percent at 30° C. of about 76,000 cps is used and the gel rigidity found to be found to be within the range of about 20 to about 800 gram Bloom.

EXAMPLE XIV-m

Compositions of Example II are continuously extruded into 1 meter length rod shape articles through a 0.05, a 0.1, a 0.2, a 0.4, a 0.8, a 1.0, a 1.5, a 1.8, a 2.0, a 4.0, a 8.0 cm (inside diameter) pipe and the extruded articles are allowed to cool to room temperature. Light from a Spectra Physics Model 155A laser with a wavelength of about 632.80 nm is introduced at one end of each article and the light transmitted therethrough.

EXAMPLE XIV-n

Example II is repeated except a high viscosity star-shaped poly(styrene-ethylene-butylene) block copolymer having a S:EB ratio of 30:70 and a Brookfield Viscosity at 25 weight percent at 25° C. of about 9000 cps is used and the gel rigidity found to be found to be within the range of about 20 to about 800 gram Bloom.

EXAMPLE XIV-o

Example II is repeated except a high viscosity star-shaped poly(styrene-ethylene-propylene) random copolymer having a S:EP ratio of 35:65 and a Brookfield Viscosity at 25 weight percent at 25° C. of about 20,000 cps is used and the gel rigidity found to be found to be within the range of about 20 to about 800 gram Bloom.

EXAMPLE XIV-p

Example II is repeated except the molten composition is casted onto a polyether, a polyester, a surlyn ionomer open cell sponge thereby displacing the air space within the sponge and the gel rigidity is found to be greater than about the sum of the combined rigidity of the composition and sponge alone.

EXAMPLE XIV-q

Example II is repeated except a high viscosity star-shaped mixed poly(styrene-ethylene-propylene) copolymer having a S:EP ratio of 35:65 and a Brookfield Viscosity at 25 weight percent at 25° C. of about 12,000 cps is used and the gel rigidity found to be found to be within the range of about 20 to about 800 gram Bloom.

EXAMPLE XIV-r

Example II is repeated except a high viscosity star-shaped mixed poly(styrene-ethylene-butylene) block copolymer having a S:EB ratio of 35:65 and a Brookfield Viscosity at 25 weight percent at 25° C. of about 9,000 cps is used and the get rigidity found to be found to be within the range of about 20 to about 800 gram Bloom.

EXAMPLE XIV-s

The composition of Example XXI is casted unto a SCOTFOAM® 1/8" thick: 5, 10, 15, 20, 25, 30, 35, 40, 45, 50, 60, 70, 80, 90, 100, and 200 ppi foam sheet.

EXAMPLE XIV-t

The procedure of Example II is repeated except Shell Kraton G 1855X, poly(styrene-ethylene-butylene-styrene)

triblock copolymer is used having a styrene end block to ethylene and butylene center block ratio of about 27:73 and the gel rigidity is found to be within the range of about 10 to about 800 gram Bloom.

EXAMPLE XV

Examples I-XIV, XIV-I,n,o,q,r and t are repeated and the gels are extruded and rapidly stretched up to 800% elongation by hand in a cooled water bath. The resulting gels show birefrigence and greater strength than corresponding unstressed (unstretched) gels.

EXAMPLE XVI

A gelatinous elastomer composition of 100 parts of Kraton G1651 and 400 parts by weight of Duraprime 200 white oil is made according to Example II and extruded and drawn into selected lengths of varying diameters from about 0.01 cm to about 0.25 cm for use as dental floss, the gel rigidity being within the range of about 20 to about 800 gram Bloom.

EXAMPLE XVII

Example XVI is repeated using Kurarary SEPS 2006 copolymer, Kurarary SEEPS 4055 copolymer, a high viscosity $(SEB)_n$ copolymer, and a high viscosity $(SEP)_n$ copolymer, the gel rigidities being within the range of about 20 to about 800 gram Bloom.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims.

What I claim is:

1. A composite article comprising a thermoplastic, heat formable and heat reversible gelatinous elastomer composition, G, which is formed into a composite by heat with one or more of a selected substrate material, M, said gelatinous elastomer composition formed from
   (i) 100 parts by weight of one or a mixture of two or more of a hydrogenated styrene isoprene/butadiene block copolymers(s) and from
   (ii) about 300 to about 1,600 parts by weight of a plasticizing oil; and in combination with or without
   (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said composite formed from the combination $G_nM_n$, $G_nM_nM_nG_n$, $G_nG_nM_nM_n$, $G_nM_nG_nM_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nMnG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

2. A composite article comprising a thermoplastic, heat formable and heat reversible gelatinous elastomer compositions, G, which is formed into a composite by heat with one or more of a selected substrate material, M, said gelatinous elastomer composition formed from
   (i) 100 parts by weight of one or a mixture of two or more of a hydrogenated styrene isoprene/butadiene block copolymer(s) and
   (ii) from about 300 to about 1,600 parts by weight of an plasticizing oil; in combination with or without
   (iii) a selected amount of one or more polymer or copolymer of poly(styrene-butadiene-styrene), poly(styrene-butadiene)$_n$, poly(styrene-isoprene-styrene), poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, branched, star-shaped, or multiarm copolymer, and n is an integer greater than one; wherein said composite formed from the combination $G_nM_n$ of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

3. A composite article comprising a thermoplastic, heat formable and heat reversible gelatinous elastomer compositions, G, which is formed into a composite by heat with one or more of a selected substrate material, M, said gelatinous elastomer composition formed from
   (i) 100 parts by weight of one or a mixture of two or more of a hydrogenated styrene block copolymer(s) with 2-methyl-1,3-butadiene and 1,3-butadiene and
   (ii) from about 300 to about 1,600 parts by weight of an plasticizing oil: in combination with or without
   (iii) a selected amount of one or more selected polymer or copolymer selected from the group consisting of poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, branched, star-shaped, or multiarm copolymer; and n is an integer greater than one, wherein said gelatinous elastomer compositions characterized by a gel rigidity of from about 20 to about 800 gram Bloom; wherein said composite formed from the combination $G_nM_n$, $G_nM_nM_nG_n$, $G_nG_nM_nM_n$, $G_nM_nG_nM_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

4. A composite article comprising a thermoplastic, heat formable and heat reversible gelatinous elastomer composition, G, which is formed into a composite article by heat with a selected substrate material M, said gelatinous elastomer composition form from
   (i) 100 parts by weight of one or a mixture of two or more of a hydrogenated styrene isoprene/butadiene block copolymer(s), wherein at least one of said block copolymer is a high viscosity copolymer having a viscosity value at 5 weight percent solution in toluene at 30° C. of about 90 cps and higher which corresponds to a viscosity at 10 weight percent of about 5800 cps and higher which corresponds to a viscosity at 20 weight percent solids solution in toluene at 25° C. of at about 80,000 cps and higher, and
   (ii) from about 300 to about 1,600 parts by weight of an plasticizing oil, and in combination with or without
   (ii) a selected amount of one or more polymers or copolymers of poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, branched, radial, star-shaped, or multiarm copolymer; and n is an integer greater than one; wherein said composite formed from the combination $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nM_nG_n$, $G_nG_nM_nG_nM_nG_n$, a sequential addition or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

5. A composite of claim 1, 2, 3, or 4, wherein said hydrogenated styrene block copolymer is one or more of a block copolymer of poly(styrene-ethylene-ethylene-propylene-styrene).

6. A composite article of claim 1 or 4, wherein a source of said hydrogenated poly(styrene-isoprene/butadiene-styrene) block polymer being Septon 4055.

7. A composite of claim 1, 2, 3, or 4, wherein said one or more (i) block copolymer(s) is poly(styrene-ethylene-ethylene-propylene-styrene) and a source of said block copolymers being Septon® 4033, Septon® 4045 and Septon® 4055.

8. A composite of claim 2, 3, or 6 wherein said thermoplastic, heat formable and heat reversible gelatinous elastomer composition is a dielectric encapsulant of an electrical, or an electronic component(s).

9. A composite article comprising a thermoplastic, heat formable and heat reversible gelatinous elastomer composition, G, which is formed into a composite article by heat with a selected substrate material M, said gelatinous elastomer composition form from
   (i) 100 parts by weight of one or a mixture of two or more poly(styrene-ethylene-ethylene-propylene-styrene) block copolymers and a source of said block copolymers being Septon® 4033, Septon® 4045 and Septon® 4055, and
   (ii) from about 300 to about 1,600 parts by weight of an plasticizing oil, and in combination with or without
   (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; wherein said composite formed from the combination $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

10. A composite article comprising a thermoplastic, heat formable and beat reversible gelatinous elastomer compositions, G, which is formed into a composite by beat with one or more of a selected substrate material, M, said gelatinous elastomer composition formed from
   (i) 100 parts by weight of a block copolymer of one or a mixture of two or more poly(styrene-ethylene-ethylene-propylene-styrene block copolymers and a source of said block copolymers being Septon® 4033, Septon® 4045 and Septon® 4055, and
   (ii) from about 300 to about 1,600 parts by weight of an plasticizing oil; wherein said composite formed from the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

11. A composite article comprising a thermoplastic, heat formable and heat reversible gelatinous elastomer compositions, G, which is formed into a composite by heat with one or more of a selected substrate material, M, said gelatinous elastomer composition formed from
   (i) 100 parts by weight of one or a mixture of two or more poly(styrene-ethylene-ethylene-propylene-styrene)

block copolymers and a source of said block copolymers being Septon® 4033 and Septon® 4055, and (ii) from about 300 to about 1,600 parts by weight of an plasticizing oil, and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; wherein said gelatinous elastomer composition characterized by a gel rigidity of from about 20 to about 800 gram Bloom; wherein said composite formed from the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

12. A composite according to claims 1, 2, 3, or 4, wherein said one or more (i) block copolymers is made from poly(styrene-ethylene-ethylene-propylene-styrene) and a source of said block copolymers being Septon® 4033 and Septon® 4055.

* * * * *

US006552109C1

(12) EX PARTE REEXAMINATION CERTIFICATE (8385th)

United States Patent
Chen

(10) Number: US 6,552,109 C1
(45) Certificate Issued: Jul. 5, 2011

(54) GELATINOUS ELASTOMER COMPOSITIONS AND ARTICLES

(75) Inventor: John Y. Chen, Pacifica, CA (US)

(73) Assignee: Patent & License Office, Pacifica, CA (US)

Reexamination Request:
No. 90/010,685, Sep. 16, 2009

Reexamination Certificate for:
Patent No.: 6,552,109
Issued: Apr. 22, 2003
Appl. No.: 08/612,586
Filed: Mar. 8, 1996

Related U.S. Application Data

(63) Continuation-in-part of application No. PCT/US94/04278, filed on Apr. 19, 1994, and a continuation-in-part of application No. PCT/US94/07314, filed on Jun. 27, 1994, and a continuation-in-part of application No. 08/288,690, filed on Aug. 11, 1994, now Pat. No. 5,633,286, and a continuation-in-part of application No. 08/581,188, filed on Dec. 29, 1995, now abandoned, and a continuation-in-part of application No. 08/581,191, filed on Dec. 29, 1995, now Pat. No. 5,760,117, and a continuation-in-part of application No. 08/581,125, filed on Dec. 29, 1995, now Pat. No. 5,962,572.

(51) Int. Cl.
*B61C 15/00* (2006.01)
*C08J 5/02* (2006.01)
*C08K 5/01* (2006.01)
*C08K 5/00* (2006.01)

(52) U.S. Cl. ............... 524/270; 428/537.1; 428/688; 428/319.3; 428/319.7; 428/319.9; 428/378; 428/441; 428/462; 428/521; 442/59; 524/474; 524/476; 524/490; 524/505; 132/321; 174/137 A; 174/137 B

(58) Field of Classification Search ............... None
See application file for complete search history.

(56) References Cited

U.S. PATENT DOCUMENTS

| | | | |
|---|---|---|---|
| 3,265,765 A | 8/1966 | Holden et al. | |
| 3,676,387 A | 7/1972 | Lindlof | |
| 3,799,775 A | * 3/1974 | Petruzzelle | 430/63 |
| 3,827,999 A | 8/1974 | Crossland | |
| 4,369,284 A | 1/1983 | Chen | |
| 4,389,587 A | * 6/1983 | Levine et al. | 310/208 |
| 4,618,213 A | 10/1986 | Chen | |
| 4,716,183 A | 12/1987 | Gamarra et al. | |
| 4,798,853 A | 1/1989 | Handlin | |
| 4,842,931 A | 6/1989 | Zook | |
| 4,880,878 A | 11/1989 | Hines | |
| 4,987,194 A | 1/1991 | Maeda et al. | |
| 5,153,254 A | * 10/1992 | Chen | 524/505 |
| 5,239,723 A | 8/1993 | Chen | |
| 5,262,468 A | 11/1993 | Chen | |
| 5,324,222 A | 6/1994 | Chen | |
| 5,336,708 A | 8/1994 | Chen | |
| 5,436,295 A | 7/1995 | Nishikawa et al. | |
| 5,442,004 A | 8/1995 | Sutherland et al. | |
| 5,475,890 A | 12/1995 | Chen | |
| 5,508,334 A | 4/1996 | Chen | |
| 5,603,122 A | 2/1997 | Kania | |
| 5,618,882 A | 4/1997 | Hammond et al. | |
| 5,624,294 A | 4/1997 | Chen | |
| 5,633,286 A | 5/1997 | Chen | |
| 5,655,947 A | 8/1997 | Chen | |
| 5,728,168 A | 3/1998 | Laghi | |
| 5,760,117 A | 6/1998 | Chen | |
| 5,830,237 A | 11/1998 | Kania | |
| 5,834,559 A | 11/1998 | Keguchi et al. | |
| 5,868,597 A | 2/1999 | Chen | |
| 5,962,572 A | 10/1999 | Chen | |
| 6,033,283 A | 3/2000 | Chen | |
| 5,633,286 A | 10/2000 | Chen | |
| 6,148,830 A | 11/2000 | Chen | |
| 6,406,499 B1 | 6/2002 | Kania | |
| 6,964,688 B1 | 11/2005 | Kania | |
| 7,291,182 B1 | 11/2007 | Kania | |

FOREIGN PATENT DOCUMENTS

| | | |
|---|---|---|
| EP | 108518 A2 * | 5/1984 |
| EP | 88306357.0 | 8/1989 |
| EP | 89118513.4 | 4/1990 |
| EP | 89311603.1 | 6/1990 |
| EP | 1618858 B1 | 9/2008 |
| WO | WO 88/00603 | 1/1988 |
| WO | WO 91/05014 | 4/1991 |
| WO | WO 93/23472 | * 11/1993 |
| WO | WO 94/18273 | 8/1994 |
| WO | WO 96/29033 | 9/1996 |

OTHER PUBLICATIONS

Septon Technical Information G–3–4 Dec. 3, 1992 Kuraray Co., Ltd., Property of Septon–4055, Septon 8008/oil Compound.
US Securities Exchange Commission Form 10–K Dec. 31, 2004 Langer, Inc. pp. 1,4, & 24.
Kania Declaration in Reexam 90/008,277 From Pair File Dec. 28, 2007 pp. 1–5.
Antec '99 Proceedings Deited by SPE Staff/pp. 1725. PW–90 Oil (1999).
Kraton Typical Property Guide SC 68–79 May 1979.
Technical Bulletin Shell Chemical Co SC:1102–89 Apr. 1989.
Kuraray SEP/SEPS Typical properties of SEP/SEPS Development products Chart: 4055 SEPS (17 sheets: some original page numbers missing) 1991.
High–Performance Thermoplastic Rubber Septon Kuraray Co, Ltd. Typical Properties Chart: 4055 SEPS, Aug. 1995 8.95(4,000).
Material Safety Data Sheet Kuraray Septon No. KIP–110US Feb. 7, 1997 Hydrogenated styrene isoprene/butadiene block copolymer CAS # 132778–07–5.

(Continued)

*Primary Examiner*—Alan Diamond

(57) ABSTRACT

Novel gelatinous compositions and articles are formed from an intimate melt blend admixture of one or more of a high viscosity poly(styrene-ethylene-butylene-styrene), poly(styrene-ethylene-ethylene-propylene-styrene), poly(styrene-ethylene-butylene)$_n$, and poly(styrene-ethylene-propylene)$_n$ triblock and branched copolymers and high levels of a plasticizing oil.

OTHER PUBLICATIONS

Material Safety Data Sheet Kuraray Septon–4033 No. KIP–107US Feb. 7, 1997 Hydrogenated styrene isoprene/butadiene block copolymer CAS# 132778–07–5.

Material Safety Data Sheet Kuraray Septon–2005 No. KIP–93 Apr. 25, 1991 Hydrogenated styrene isoprene block copolymer.

Material Safety Data Sheet Kuraray Septon–2006 No. KIP–94 Apr. 25, 1991 Hydrogenated styrene isoprene block copolymer.

Material Safety Data Sheet Kuraray Septon–4055 No. KIP–95 Apr. 25, 1991 Hydrogenated styrene isoprene/butadiene block copolymer.

Material Safety Data Sheet Kuraray Septon–8006 No. KIP–106 Jan. 12, 1993 Hydrogenated styrene butadiene block copolymer.

Prosthetics/Orthotics Silipos Advanced Polymer Technology of SEBS tri–block polymer gel product catalogue (4 bi–folds Knit–Rite distribution data of 1993).

Silipos Manual by Robert Mogel & Peter Bickel (26 pages).

Requester (Mark R. Engle) prepared VI List Reference Appendix BB of Reexamination Request 90/010,837 (Bates No. KUR0116–117) of Affidavit of Harum ASA DOI of Oct. 11, 2006.

Septon Technical Information G–18, Sep. 17, 1992, Kuraray Co., Ltd.

Septon Technical Information G–3–4, Dec. 3, 1992, Kuraray Co., Ltd.

Holden, Geoffrey, et al., Thermoplastic Elastomers, 2nd Edition, pp. 1–3 and 48–65, Hanser/Gardner Publications, Inc., Cincinnati, 1996.

CRC Handbook of Chemistry and Physics, 70th Edition, 1989–1990, pp. C–161–162 and C–329, Chemical Rubber Publishing Company, US.

Material Safety Data Sheet, Kuraray Co., Ltd., Kuraray Septon 4055, Apr. 25, 1991, Tokyo, Japan.

High–Performance Thermoplastic Rubber, Septon™, Kuraray Co., Ltd., Aug. 1995, Tokyo, Japan.

Thermoplastic Elastomer Gels. I Effects of Composition and Processing on Morphology and Gel Behavior, Laurer, et al., J. of Poly. Sci.: Part B. Poly. Phys. V. 36 (1998).

Thermoplastic Elastomer Gels, I Effects of Composition and Temperature on Morphology and Gel Rheology, Laurer, et. al., J. of Poly. Sci.: Part B. Pol. Phys. V. 36 (1998).

Morphology and Rheology of SIS and SEPD Triblock Copolymers in the Presene of a Midblock Selective Solvent, Laurer, et al., Web Sep. 24, 1999.

Viscoelastic and Gelation Studies of SEBS Thermoplastic Elastomer in Different Hydrocarbgon Oils, J. F. Kim, et. al., Macromolecular Rech. V. 14, #3 (2006).

* cited by examiner

US 6,552,109 C1

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 10, after line 49:

*An example of the above mentioned toy is a Humdinger spinning toy of the related co-pending filed patent application U.S. Ser. No. 08/211,781 filed PCT on Apr. 19, 1994, now U.S. Pat. No. 6,033,283 and incorporated in U.S. Pat. No. 6,552,109 by reference, which describes the structure and operation of Humdinger spinning toy as follows:*

*When a gel body is set into rotation of at least 100 r.p.m. (revolutions per minute) to as high as 1,000 r.p.m. and higher, the forces can be significant. The following examples can best illustrate the forces involved.*

*The inward pulling forces generated by a pair of twisting stings as measured on a spring scale for a 2.00" (5.08 mm) dia. times, 0.50" (12.70 mm) thickness spinning circular gel body can range from an extreme of less than one pound to forty pounds and greater. The typical range for such a spinning gel body may range from between less than five pounds to twenty pounds and greater. As another example, the measured pulling forces for a (smaller) 1.75" (44.46 mm) diameter times 0.60" (15.24 mm) spinning circular gel body can range from an extreme of less than one pound to twenty five pounds and greater. The typical range for such a smaller body is between less than three pounds to about eight pounds and greater.*

*For the purpose of the invention, an indirect measure of the shearing forces generated during play is measured (in pounds) by the inward pulling forces of the twisting strings 5 on a spring balance during dynamic spinning. The typical values can range from less than one pound to fifty pounds and greater. String puling forces for various shapes (large and small) of spinning bodies having measured values of 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 . . . 40, 50, 60 ,70, 80 pounds and greater can be achieved and such values are typical. During spinning, the measured pulling force is read as a dynamic measurement which starts from a low value and rise as the string(s) are pulled apart forcing the body to reaching a maximum spin rate (i.e. maximum measured pulling force value).*

*The dynamic variables due to the centrifugal force of rotation of the bodies, such as elongation, stress and shear forces, under extreme high torque conditions, and the accelerations and de-accelerations involved are ever changing during play.*

*The bodies of the invention when rotated about an axis of rotation will experience increased deformation from their original shapes with increasing rates of rotation. Irrespective of the original shapes of the bodies, when subjected to rotational forces, the bodies will deform in a highly elastic, predetermined, non-uniform, and non-radial manner. Because of the high deformations resulting from rotational forces, the bodies will distribute their mass outwardly by elongating perpendicularly with respect to its axis of rotation. The gel material at the extreme outer parts (equator) of the bodies will experience greater and greater centrifugal force as the bodies rotate and elongate more and more. The bodies if not properly designed will be pulled apart by the increasing centrifugal force of rotation. For example, the centrifugal force of a rotating body having a mass of about 50 grams and an elongated mass about the body's equator of about 10 centimeters may produce from less than about 50 to about 250 pound-force or higher.*

*If the hole separation distance is zero, then the torque will also be zero. Therefore, a suitable separation distance is needed to separate the holes from each other and the holes 6 from the selected axis of rotation. The holes should be separated approximately equal distance from the axis of rotation. A suitable distance, x, may be selected based on various factors, including the moment of inertia, axis of rotation, and the necessary torque need to rotate the bodies about its axis of rotation by the action of the twisting string. If the separation between the holes with respect to the axis of rotation is slightly off, then the torque applied to the bodies will be unbalanced. The unbalanced rotation would not be totally disastrous, but may produce a desirable off-balanced effect. While the humdinger may still adequately operate, it will be more difficult to keep the wobbling humdinger rotating in the unbalanced state.*

*As the bodies rotate, the moment of inertia will change and the point of the applied torque will also change. The moment of inertia of the bodies changes because the shape of the bodies changes with increased rate of rotation. Due to the highly elastic nature of the gel bodies, as their shape changes, so will the position of the holes with respect to each other and with respect to their distances from the axis of rotation. Any off-centering of the placement of the holes with respect to the axis of rotation will be greatly magnified by the centrifugal force acting on the body, since the original placement of the holes will also be changed due to elastic stretching. The torque acting on the bodies will greatly vary as the centrifugal force futher separates the holes from each other and from the axis of rotation.*

*Moreover, the overall original shape of a body will also affect the position of the holes, as the body is set into rotation. The change in separations between the holes and the change in distance between the holes and the axis of rotation due to the centrifugal force acting on the body is also affected by the shape of the original body as a whole. In other words, the configuration of the original shape of the elastic body directly affects the amount and direction of the elastic deformation about the holes caused by the centrifugal force. A stretching or elastic deformation of one part of a body will directly affect other parts of the body as well. Therefore, any deformation by an applied force on any part of the body will correspondingly cause deformation to other parts of the body. The holes and the shape of the bodies are always in a state of flux due to the forces generated during rotation. The holes freely move about as the shape of the body is changed by the force of rotation. This is the nature of bodies under dynamic motion as opposed to rigid bodies.*

*The string is passed through the two holes of the gel body and tied into a loop. For gel bodies having three or more holes, the individual strings may be passed through the holes and tied together at opposite ends. The gel body is set into continuous alternating rotating motion with an initial twirl of the body followed by alternately pulling and releasing the string while holding it in opposite directions which keeps it* spinning. Between the second and fourth full reversal of rotation of the gel body, the string will have sufficient twist to shear off, and cut into or through the gel material separating the holes. Gel material of low strength cannot resist the tremendous shearing action of the twisting strings between the holes. The twisting action of the strings generated by the spinning gel body can exhibit a first order twist, a second order twist, or higher order twists. A first order twist refers to one or more twists of a pair of strings (i.e. a pair of strings when twisted together forms a small tight binding helix). A second order twist refers to one or more large binding helixes built up by a pair of strings that have been twisted beyond the maximum number of twists which normally produces small tight binding helixes of the first order kind. Similarly, a third order twist refers to a much larger tightly binding helix built up by the maximum number of second order twists produced by the pair of twisting strings. The third order twist may be manifested by the appearance of a branch of two or more twist of the first order twisting strings.

The shear force created by the static twisiting of the string, however, is substantially different than the shear force generated under dynamic twisting of the strings. This can be demonstrated by taking a sample of any of the soft gel bodies and subject it to static twisting between a pair of strings under a static spring load of 20, 30, and 40 lbs for twenty four hours and compare the condition of the sample to samples of the same gel body subject under dynamic twist spring load of less than 20 lbs. (e.g. 5, 8, 10, 12, 16, 18, etc.). The results show that the shear force produce by a dynamic twist spring load of less than 20 lbs will easily cut a soft gel body or any low strength material body while the same sample will remain substantially uncut under a higher static twist spring load. Therefore, it is important to take into consideration the drastic effects of the shear force produced by the dynamic twisting of a pair of strings.

Suitable interlocking materials (that helps resist the shear force of the twisting strings) for use in the humdingers of the invention include: open cell foams, other polymeric or elastomeric (Kraton) materials, porous materials, multi-layered coatings, and single layered, and composite layered materials. As an example, an opened cell foam when dipped into the instant composition will form an interpenetrating physical networks (interlocking of gel composition and foam composite). Such composite will exhibit greater rigidity and resistance to the shear force generated by a first, a second, a third, or a higher order dynamic twisting of a pair of strings. Furthermore, the interlocking materials surrounding the holes of the gel bodies may be made from flexible materials, such as fibers and fabrics of cotton, flax, and silk. Other flexible materials include: elastomers, fiber-reinforced composites, mohair, and wool. Useful synthetic fibers include: acetate, acrylic, aramid, glass, modacrylic polyethylene, nylon, olefin, polyester, rayon, spandex, carbon, sulfar, polybenzimidazole, and combinations of the above.

The following commercial elastomers can be formed with oil and in combination with other polymers into suitable gels for use in making the bodies of the invention, which includes Kuraray (SEP), (SEPS) or (SEB/EPS) Nos. 1001 (SEP), 2002 (SEPS), 2063 (SEPS), 2023 (SEPS), 2043 (SEPS), 2063 (SEPS), 2005 (SEPS), 2006 (SEPS), 2050 (SEPS), 2103 (SEPS), 2104 (SEPS), 2105 (SEPS), and 4055 (SEB/EPS) (styrene-ethylene-butylene/ethylene-propylene-styrene) block polymer made from hydrogenated styrene isoprene/butadiene styrene block copolymer or more specifically made from hydrogenated styrene block polymer with 2-methyl-1,3-butadiene and 1,3-butadiene. Where the ethylene (E) of the ethylene-butylene (EB) segment of the midblock (EB/EP) of the (SEB/EPS) block polymer is substantially greater than butylene (B) so as to exhibit ethylene crystallinity, (SEP/EPS) may be denoted as (SE/EPS) or denoted as (SEEPS) block polymer for the sake of simplicity.

In the operation of the humdingers of the invention, the string's twisting action imparts rotation to the gel body so as to elongate the gel body during rotation. The elongated gel body will reach a maximum elongation due to centrifugal force of 50% or more. Elongations of 100%, 200%, 300%, 400%, 500%, 600%, 700% and higher are possible depending on the amount of tension of the pull of the humdinger's strings. Gel bodies of the invention can be designed to withstand elongations higher than 1,000%, which can occur at extreme high rates of rotation of 500 r.p.m. and higher. Spinning rates can span from a low of 10 r.p.m. to a high of over 1,000 r.p.m. Spinning rates of 50, 100, 150, 200, 25, 300, 350, 400, 500, 600, 700, 800, 900, 1,000, 1,200, and 1,400 r.p.m. values are routinely achieved.

The operation of the humdingers of the invention can be ready observed under strobe light. The number of revolutions per minute may be counted in this way. The changes in radius can be measured. The change in gel body shape can be observed and measured. The centrifugal force acting on the rotating gel body can be likewise determined at any instant of time, at any instant rate of rotation, and at any instant change in gel body shape. The perpendicular-axis elongation effect of the gel body can be viewed under strobe light; its regions of deformation and re-distribution of mass can be viewed, measured and readily determined by ruled grid markings on the gel body.

AS A RESULT OF REEXAMINATION, IT HAS BEEN DETERMINED THAT:

Claims 1-11 are determined to be patentable as amended.

Claim 12, dependent on an amended claim, is determined to be patentable.

New claims 13-16 are added and determined to be patentable.

1. A composite article comprising a thermoplastic, heat formable and heat reversible gelatinous elastomer composition, G, which is formed into a composite by heat *and physically interlocked* with one or more of a selected substrate material, M, said gelatinous elastomer composition formed from (i) 100 parts by weight of one or a mixture of two or more of a hydrogenated styrene isoprene/butadiene block copolymers(s) *comprising poly(styrene-ethylene-ethylene-propylene-styrene)* and from (ii) about 300 to about 1,600 parts by weight of a plasticizing oil; and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-stryrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multi-arm copolymer, wherein n is greater than one; and wherein said composite formed from the combination $G_nM_n$, $G_nM_nM_nG_n$, $G_nG_nM_nM_n$, $G_nM_nG_nM_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_nG_n$ $M_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or different gel rigidity.

2. A composite article comprising a thermoplastic, heat formable and heat reversible gelatinous elastomer compositions, G, which is formed into a composite by heat *and physically interlocked* with one or more of a selected substrate material, M, said gelatinous elastomer composition formed from (i) 100 parts by weight of one or a mixture of two or more of a hydrogenated styrene isoprene/butadiene block copolymer(s) *comprising poly(styrene-ethylene-ethylene-propylene-styrene)* and (ii) from about 300 to about 1,600 parts by weight of an plasticizing oil; in combination with or without (iii) a selected amount of one or more polymer or copolymer of poly(styrene-butadiene-styrene), poly(styrene-butadiene)$_n$, poly(styrene-isoprene-styrene), poly(styrene-isoprene)$_n$, poly(stryene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radical, branched, star-shaped, or multiarm copolymer, and n is an integer greater than one; wherein said composite formed from the combination $G_nM_n$ of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

3. A composite article comprising a thermoplastic, heat formable and heat reversible gelatinous elastomer compositions, G, which is formed into a composite by heat *and physically interlocked* with one or more of a selected substrate material, M, said gelatinous elastomer composition formed from (i) 100 parts by weight of one or a mixture of two or more of a hydrogenated styrene block copolymer(s) with 2-methyl-1,3-butadiene and 1,3-butadiene *comprising poly(styrene-ethylene-ethylene-propylene-styrene)* and (ii) from about 300 to about 1,600 parts by weight of an plasticizing oil: in combination with or without (iii) a selected amount of one or more selected polymer or copolymer selected from the group consisting of poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ehtylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, branched, star-shaped, or multiarm copolymer; and n is an integer greater than one, wherein said gelatinous elastomer compositions characterized by a gel rigidity of from about 20 to about 800 gram Bloom; wherein said composite formed from the combination $G_nM_n$, $G_nM_nM_nG_n$, $G_nG_nM_nM_n$, $G_nM_nG_nM_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $M_nG_nM_n$, $G_nM_nG_nG_n$, $G_nM_nM_nG_n$, $G_nG_nM_nM_n$, $G_nG_n$-$M_nG_nM_n$, $G_nM_nG_nM_nM_n$, $M_nM_nG_nM_nG_nM_nG_n$, $G_nG_nM_n$ $M_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

4. A composite article comprising a thermoplastic, heat formable and heat reversible gelatinous elastomer composition, G, which is formed into a composite article by heat *and physically interlocked* with a selected substrate material M, said gelatinous elastomer composition form from (i) 100 parts by weight of one or a mixture of two or more of a hydrogenated styrene isoprene/butadiene block copolymer(s) *comprising poly(styrene-ethylene-ethylene-propylene-styrene)*, wherein at least one of said block copolymer is a high viscosity copolymer having a viscosity value at 5 weight percent solution in toluene at 30° C. of about 90 cps and higher which corresponds to a viscosity at 10 weight percent of about 5800 cps and higher [which corresponds to a viscosity at 20 weight percent solids solution in toluene at 25° C. of at about 80,000 cps and higher], and (ii) from about 300 to about 1,600 parts by weight of an plasticizing oil, and in combination with or without (ii) a selected amount of one or more polymers or copolymers of poly(styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, branched, radial, star-shaped, or multiarm copolymer; and n is an integer greater than one; wherein said composite formed from the combination $G_nM_n$, $G_nM_nG_n$, $M_nG_nM_n$, $G_nG_nM_n$, $M_nM_nM_nG_n$, $M_nM_n$-$M_nG_nM_n$, $M_nG_nG_nM_n$, $G_nM_nG_nG_n$, $G_nM_nM_nG_n$, $G_nG_nM_nM_nM_n$, $G_nG_nM_nG_nM_n$, $G_nM_nG_nM_nM_n$, $M_nG_nM_nG_n$-$M_nG_n$, $G_nG_nM_nM_nG_n$, $G_nG_nM_nG_nM_nG_n$, a sequential addition or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

5. A composite of claim 1, 2, 3, or 4, wherein said [hydrogenated styrene] block [copolymer] *copolymer(s)* is one or more of a block copolymer of poly(styrene-ethylene-ethylene-propylene-styrene).

6. A composite article of claim 1 or 4, wherein a source of said [hydrogenated poly(styrene-isoprene/butadiene-styrene)] block [polymer] *copolymer(s)* being [Septon] *Septon® 4055*.

7. A composite of claim 1, 2, 3, or 4, wherein said *source of* one or more (i) block copolymer(s) [is] *of* poly(styrene-ethylene-ethylene-propylene-styrene) [and a source of said block copolymers] being *of the group* Septon® 4033, Septon® 4045 and Septon® 4055.

8. A composite *article* of claim 2, 3, or [6] *4* wherein said thermoplastic, heat formable and heat reversible gelatinous elastomer composition is a dielectric encapsulant of an electrical, or an electronic component(s); *wherein said electrical or said electronic component(s) are not a said substrate material $M_n$ being physically interlocked with said $G_n$ forming said composite article.*

9. A composite article comprising a thermoplastic, heat formable and heat reversible gelatinous elastomer composition, G, which is formed into a composite article by heat *and physically interlocked* with a selected substrate material M, said gelatinous elastomer composition form from (i) 100 parts by weight of one or a mixture of two or more poly(styrene-ehtylene-ethylene-propylene-styrene) block copolymers and a source of said block copolymers being *of the group* Septon® 4033, Septon® 4045 and Septon® 4055, and (ii) from about 300 to about 1,600 parts by weight of an plasticizing oil, and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; wherein said composite formed from the combination $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$, wherein when n is a subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

10. A composite article comprising a thermoplastic, heat formable and beat reversible gelatinous elastomer compositions, G, which is formed into a composite by [beat] *heat and physically interlocked* with one or more of a selected substrate material, M, said gelatinous elastomer composition formed from (i) 100 parts by weight of a block copolymer of one or a mixture of two or more poly(styrene-ethylene-ethylene-propylene-styrene block copolymers and a source of said block copolymers being *of the group* Septon® 4033, Septon® 4045 and Septon® 4055, and (ii) from about 300 to about 1,600 parts by weight of an plasticizing oil; wherein said composite formed from the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nG_nM_nG_n$, a sequential addition or a permutation of one or more of said $G_n$ with $M_n$; wherein when n is subscript of M, n is the same or different selected from the group consisting of foam, plastic, fabric, metal, concrete, wood, glass, ceramics, synthetic resin, synthetic fibers or refractory materials; and wherein when n is a subscript of G, n denotes the same or a different gel rigidity.

11. A composite article comprising a thermoplastic, heat formable and heat reversible gelatinous elastomer compositions, G, which is formed into a composite by heat *and physically interlocked* with one or more of a selected substrate material, M, said gelatinous elastomer composition formed from (i) 100 parts by weight of one or a mixture of two or more poly(styrene-ethylene-ethylene-propylene-styrene) block copolymers and a source of said block copolymers being *of the group* Septon® 4033 and Septon® 4055, and (ii) from about 300 to about 1,600 parts by weight of an plasticizing oil, and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; wherein said gelatinous elastomer composition characterized by a gel rigidity of from about 20 to about 800 gram Bloom; wherein said composite formed from the combination $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with $M_n$; wherein when n is a subscript of M, n is the same or different selected from the group consisting of foam, plastic, fabric, metal, concrete, wood, glass ceramics, synthetic resin, synthetic fibers or refractory materials; and wherein when n is a subscript of G, n denotes the same or a different gel ridigity.

*13. A composite article comprising a thermoplastic, heat formable and heat reversible gelatinous elastomer composition, G, which is formed into said composite article by heat and physically interlocked with one or more of a selected substrate material, M, said gelatinous elastomer composition formed from*
  *(i) 100 parts by weight of one or a mixture of two or more of a hydrogenated styrene isoprene/butadiene block copolymer(s) comprising poly(styrene-ethylene-ethylene-propylene-styrene), and from*
  *(ii) about 300 to about 1,200 parts by weight of a plasticizing oil; wherein said composite formed from the combination $G_nM_n$, $G_nM_nG_n$, $M_nG_nM_n$, a permutation of one or more of said $G_n$ with $M_n$; wherein when n is a subscript of M, n is the same or different fabric materials of the group cotton, acrylic, nylon, polyester, and spandex; and wherein when n is a subscript of G, n denotes the same or a different gel rigidity.*

*14. A composite article comprising a thermoplastic, heat formable and heat reversible gelatinous elastomer composition, G, which is formed into said composite article by heat and interlocked with one or more of a selected substrate material, M, said gelatinous elastomer composition formed from*
  *(i) 100 parts by weight of one or a mixture of two or more of a hydrogenated styrene isoprene/butadiene block copolymers(s) comprising poly(styrene-ethylene-ethylene-propylene-styrene), and from*
  *(ii) about 300 to about 1,200 parts by weight of a plasticizing oil; wherein said composite formed from the combination $G_nM_n$, $M_nG_nM_n$, a permutation of one or more of said $G_n$ with $M_n$; wherein when n is a subscript of M, n is the same or one or more different fiber materials of the group acrylic, nylon, olefin, polyester, rayon, and spandex; and wherein when n is a subscript of G, n denotes the same or a different gel rigidity.*

15. A composite article comprising a thermoplastic, heat formable and heat reversible gelatinous elastomer composition, G, which is formed into said composite article by heat with one or more of a selected substrate material, M, said gelatinous elastomer composition formed from
  (i) 100 parts by weight of one or a mixture of two or more of a hydrogenated styrene isoprene/butadiene block copolymers(s) comprising poly(styrene-ethylene-ethylene-propylene-styrene), and from
  (ii) about 300 to about 1,200 parts by weight of a plasticizing oil; wherein said composite formed from the combination $G_nM_n$, $M_nG_nM_n$, a permutation of one or more of said $G_n$ with $M_n$; wherein when n is a subscript of M, n is the same or different fabric materials; and wherein when n is a subscript of G, n denotes the same or a different gel rigidity.

16. A composite article comprising a thermoplastic, heat formable and heat reversible gelatinous elastomer composition, G, which is formed into said composite article by heat with one or more of a selected substrate material, M, said gelatinous elastomer composition formed from
  (i) 100 parts by weight of one or a mixture of two or more of a hydrogenated styrene isoprene/butadiene block copolymers(s) comprising poly(styrene-ethylene-ethylene-propylene-styrene), and from
  (ii) about 300 to about 1,200 parts by weight of a plasticizing oil; wherein said composite formed from the combination $G_nM_n$ or a permutation of one or more of said $G_n$ with $M_n$; wherein when n is a subscript of M, n is the same or different materials of the group fabric and synthetic fiber materials; and wherein when n is a subscript of G, n denotes the same or a different gel rigidity.

\* \* \* \* \*